United States Patent [19]

Mitsui et al.

[11] 4,209,508

[45] Jun. 24, 1980

[54] ANTIMICROBIAL SUBSTANCE C-3603 AND PROCESS FOR PREPARING THE SAME

[75] Inventors: Isamu Mitsui, Yokohama; Takefumi Iwanami, Kawasaki; Kazuo Joko, Tokyo; Tsutomu Watanabe, Kamakura; Motozumi Yamadaki; Yukinori Mori, both of Tokyo, all of Japan

[73] Assignee: The Calpis Food Industry Co., Ltd., Tokyo, Japan

[21] Appl. No.: 900,868

[22] Filed: Apr. 28, 1978

[30] Foreign Application Priority Data

Jul. 28, 1977 [JP] Japan .................................. 52-89790

[51] Int. Cl.$^2$ ............................................. A61K 35/00
[52] U.S. Cl. ..................................... 424/117; 435/169
[58] Field of Search ...................... 424/117; 195/80 R; 435/169

[56] References Cited

U.S. PATENT DOCUMENTS 3,819,833   6/1974   Ishida et al. .......................... 424/117

Primary Examiner—Jerome D. Goldberg
Attorney, Agent, or Firm—Browdy and Neimark

[57] ABSTRACT

Novel antimicrobial substance C-3603 was obtained from the culture of *Streptococcus mutans* C-3603, FERM-P No. 4128, ATCC No. 31383. The novel antimicrobial substance C-3603 shows a high antimicrobial activity against a variety of gram-positive bacteria, particularly cariogenic bacteria in the oral cavity and it is expected for the utilization to prevent oral infectious diseases, particularly dental caries.

2 Claims, 3 Drawing Figures

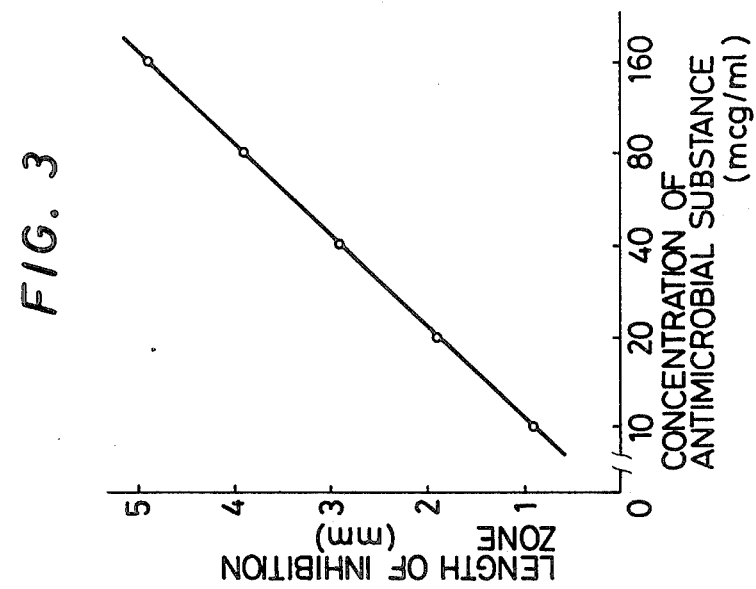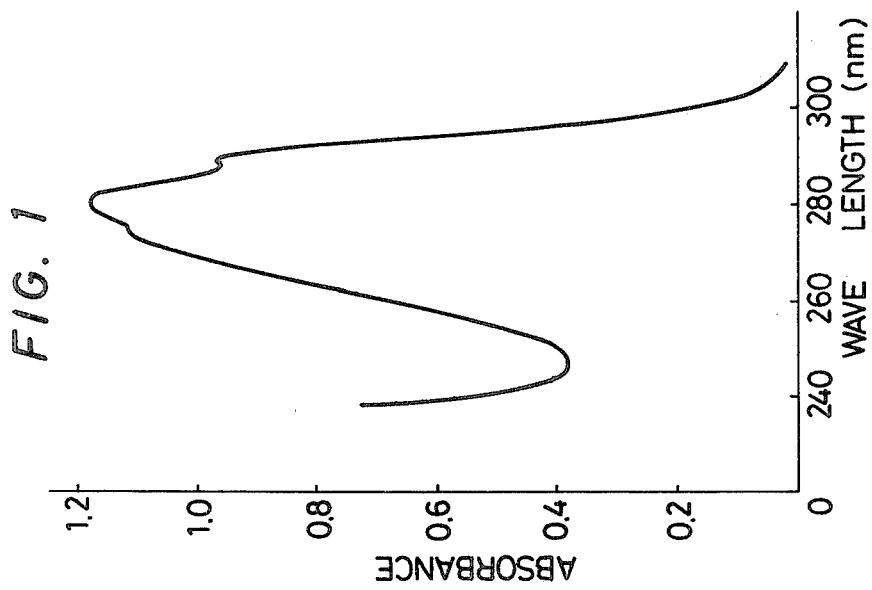

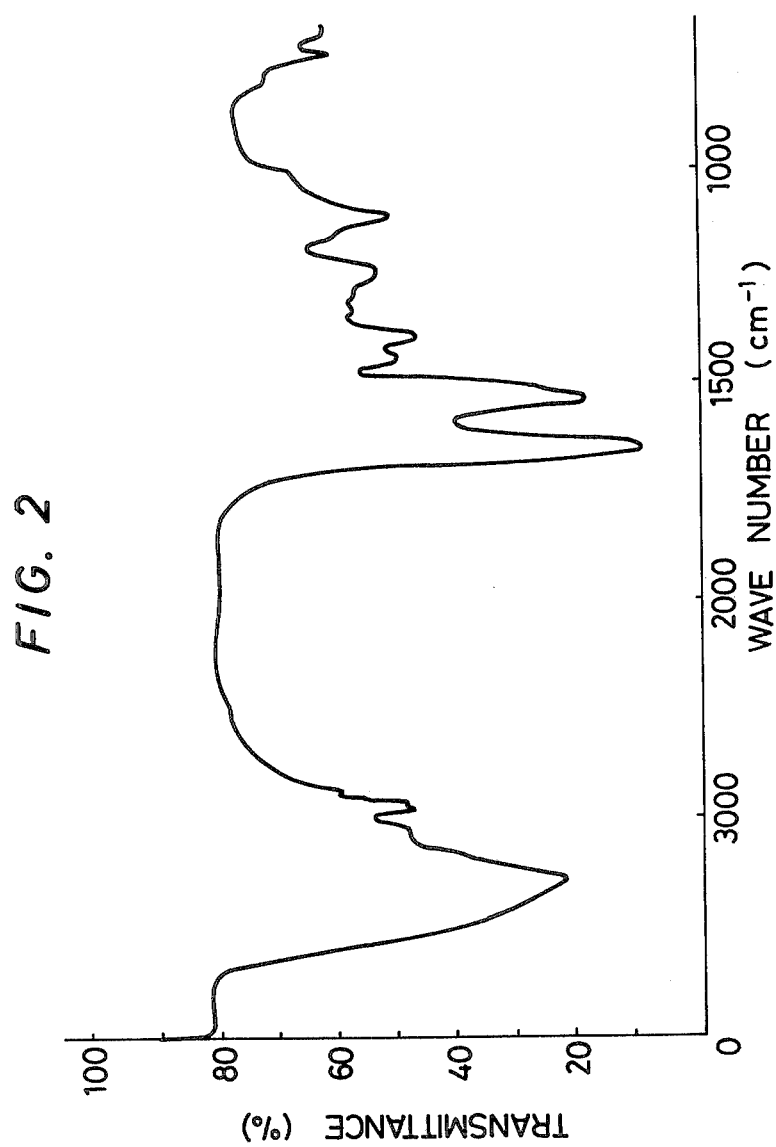

ANTIMICROBIAL SUBSTANCE C-3603 AND PROCESS FOR PREPARING THE SAME

DETAILED EXPLANATION OF INVENTION

The present invention relates to a novel antimicrobial substance C-3603 and a process for preparing the same and the gist thereof lies in cultivating a certain species of genus Streptococcus producing the antimicrobial substance C-3603 in a medium and isolating the antimicrobial substance C-3603 from the resulting culture fluid.

The novel antimicrobial substance C-3603 obtained by the present invention shows a high antimicrobial activity against a variety of gram-positive bacteria, particularly cariogenic bacteria in the oral cavity, so that it can be expected for the utilization to prevent oral infectious diseases, particularly dental caries.

Such microorganism producing the antimicrobial substance C-3603 is exemplified by the strain C-3603 of genus Streptococcus newly isolated by the inventors of the present invention, and the bacteriological properties of the strain Streptococcus C-3603 are as follows after examinating the properties shown by the strain by applying the method described in the publication of Cowan and Steel's "Manual for the Identification of Medical Bacteria", Second Edition, Cambridge University Press (1974):

I Morphological properties:

It is a gram-positive coccus having the size of 0.8–1.2 μm and it forms linked body by linking up with two to ten odd. There are not found the spore formation, the motility, the acid fast and the polymorphism.

II Cultural properties obtained on various media:

1. Mitis Salivarius agar (37° C., anaerobic culture for two days): Moderate growth, round, entire and convex.
2. Trypticase Soy agar (37° C., anaerobic culture for two days): Abundant growth, round, entire, flat and no production of pigment.
3. Brain Heart Infusion agar (37° C., anaerobic culture for two days): Abundant growth, round, entire, flat and no production of pigment.
4. GAM agar (Nissui Seiyaku, Japan) (37° C., anaerobic culture for two days): Abundant growth, round, entire, convex and no production of pigment.
5. Trypitcase Soy broth with 5% sucrose (37° C., anaerobic culture for two days): The culture was performed under an inclination of 45°, and thereby a great quantity of insoluble substance supposed to be a polysaccharide adhered at the bottom and along the lower portion under the inclined surface of a test tube.

III Physiological properties:

1. Haemolysis: None
2. Catalase activity: Negative
3. Oxidase activity: Negative
4. Growth at 45° C.: Negative
5. Temperature tolerance (60° C. for 30 min): Negative
6. Growth at pH 9.6: Negative
7. $CO_2$ requirement: Positive
8. Growth on medium containing 4% NaCl: Negative
9. Growth on medium containing 40% bile: Positive
10. Growth on medium containing 1/4000 tellurite: Negative
11. Acid from carbohydrates (Table 1):

Table 1

| Carbohydrates | Acid formation |
| --- | --- |
| D-Glucose | + |
| L-Arabinose | − |
| Glycerol | − |
| Lactose | + |
| Maltose | + |
| Mannitol | + |
| Raffinose | + |
| Salicin | + |
| D-Sorbitol | + |
| Sucrose | + |
| Trehalose | + |

12. VP (Voges-Proskauer) test: Positive
13. Aesculin hydrolysis: Positive
14. Litmus milk: Coagulation, reduction of indicator
15. Gelatin hydrolysis: Negative
16. Arginine hydrolysis: Negative
17. Hippurate hydrolysis: Negative
18. Bile solubility: Negative
19. Of (oxidation or fermentation of glucose) test: Fermentation On close examination of the above described properties referring to Cowan and Steel's "Manual for the Identification of Medical Bacteria", Second Edition, Cambridge University Press (1974), it is clearly recognized that the strain of the present invention belongs to *Streptococcus mutans*. Accordingly, said strain has been named *Streptococcus mutans* C-3603. The present strain has been deposited with the Fermentation Research Institute, Agency of Industrial Science and Technology under the deposition number of FERM-P No. 4128 and deposited with the American Type Culture Collection under ATCC No. 31383. The microorganism useful in the present invention is any antimicrobial substance C-3603 producing organism belonging to Streptococcus, not to speak of the present strain as well as spontaneous and artificial mutants thereof.

Next, a method of culturing a microorganism, for example strain C-3603 and a method of isolating the antimicrobial substance C-3603 from the culture fluid will be explained.

As a medium, various media, containing carbon source, nitrogen source, minerals, vitamins and amino acids etc. and being usually used for culturing microorganisms, can be widely used. As the carbon source, such one which contains an assimilable compound containing carbon can be all utilized, for example such as glucose, galactose, maltose, sucrose, lactose and molasses etc. As the nitrogen source, such one which contains an assimilable compound containing nitrogen can be all utilized, for example such as peptone, meat extract and acid hydrolysate of casein etc. Besides, phosphoric acid salts and salts of magnesium, sodium, potassium, calcium, iron and manganese etc., and vitamins, amino acids, antiforming agents and surface-active agents can be used when desired. As the medium a liquid medium is preferable, and the culture may be carried out either under aerobic or anaerobic conditions, but preferably the static culture under aerobic conditions is suitable. The initial pH of the medium is pH 5–9, preferably pH 7.0–8.0, and the culture temperature is 20°–42° C., preferably 35°–40° C., and the culture period is suitably of 14–72 hours.

In the culture fluid thus obtained, the principal amount of the antimicrobial substance C-3603 presents in the filtrate of the culture fluid. In order to isolate the antimicrobial substance C-3603 from the fluid from which the cells have been removed, conventional separation and purification methods generally used for separating proteins and antibiotics are appropriately utilized, and hereinafter an example thereof will be explained.

The cells are removed from the culture fluid by a centrifuge thereby obtaining a supernatant fluid. Thus obtained supernatant fluid is added with ammonium sulfate and allowed to stand at a lower temperature. The produced precipitate is collected by a centrifuge and the collected precipitate is dissolved in a small amount of phosphate buffer solution and then the supernatant fluid is obtained by a centrifuge. The supernatant solution thus obtained is passed through a CM-Sephadex column bufferized by said buffer solution to adsorb the antimicrobial substance thereon and then an alkali buffer solution is passed through the column thereby eluting the antimicrobial substance therefrom. The obtained solution is desalted by a gel filtration and the desalted solution is subjected to freeze-drying and as a result the present antimicrobial substance is obtained as a white powder.

BRIEF EXPLANATION OF DRAWINGS

FIG. 1 shows the ultraviolet absorption spectrum of the antimicrobial substance C-3603;

FIG. 2 shows the infrared absorption spectrum of said substance; and

FIG. 3 is the graph showing the relation between the concentration of antimicrobial substance and length of inhibition zone in the overlaying method.

Physical and chemical properties of the antimicrobial substance C-3603 of the present invention are as follows:

1. Elemental analysis
   (i) C: 50.01%, H: 6.19%, N: 12.84%, S: 0.96%, O (balance): 30.00%
   (ii) C: 49.80%, H: 6.30%, N: 11.41%, S: 1.18%, O (balance): 31.31%;
2. Molecular weight
   6,000–10,000 (determined by SDS-polyacrylamide gel disc electrophoresis);
3. Decomposition point
   190°–195° C.;
4. Specific rotation
   Due to high molecular weight, even if aqueous solution of acetic acid is used, a sufficient concentration can not be obtained, so that the measurement is impossible;
5. Ultraviolet absorption spectrum
   The spectrum taken in the aqueous solution is shown in FIG. 1 and it has the absorption maxima at 280 nm ($E_{1\ cm}^{1\%}$: 40) and 289 nm ($E_{1\ cm}^{1\%}$: 33);
6. Infrared absorption spectrum
   The spectrum, presented as FIG. 2, shows the absorption bands at the following wave numbers when run in a KBr disc: 3290, 1650, 1535, 1240, 1105 and 733 cm$^{-1}$;
7. Solubility to the solvent
   Slightly soluble in aqueous solution of acid (pH 3.0) and practically insoluble in water. Insoluble in methanol, ethanol, acetone, ether, acetic acid ethyl ester, chloroform, n-hexane and benzene;
8. Color reaction
   The substance reacts positively in the following color reactions: ninhydrin, biuret, xanthoprotein and Adamkiewicz;
9. Isoelectric point
   pI = 10.0 ± 0.2 (determined by polyacrylamide gel disc isoelectric separation);
10. Color and form of substance
    White powder; and
11. Analysis of amino acids An example of the result of the analysis of amino acids, in which the hydrolysate by p-toluenesulfonic acid was analysed, is shown in Table 2. Numerical values show mole percentage of each amino acid to total molar concentration of amino acids. The method of analysis was according to that of T.-Y. Liu and Y. H. Chang (J. Biol. Chem., 246, 2842, 1971).

Table 2

| Amino Acids | mole % | Amino acids | mole % |
|---|---|---|---|
| Asp. | 4.5 | Ileu. | 7.0 |
| Thr. | 2.2 | Leu. | 9.5 |
| Ser. | 4.1 | Tyr. | 3.9 |
| Glu. | 4.6 | Phe. | 6.1 |
| Pro. | 0 | Trp. | 4.5 |
| Gly. | 11.5 | Lys. | 7.7 |
| Ala. | 12.1 | His. | 0 |
| Cys. | 0 | Ammonia | 9.6 |
| Val. | 7.0 | Arg. | 3.3 |
| Met. | 2.4 | total | 100.0 |

12. Analysis of fatty acids

The hydrolysate by acid (6NHCl, 120° C., 20 hr.) was extracted by chloroform-methanol, but the fatty acids ($C_{10}$–$C_{18}$) were not detected by gas-liquid-chromatography.

Judging from the above described physical and chemical properties, the present antimicrobial substance C-3603 is presumed to be an antimicrobial substance containing peptide. Agar dilution assays done with several microorganisms give the inhibitory spectra in the following tables. Table 3 shows the inhibitory spectrum of the antimicrobial substance C-3603 on lactic acid bacteria and Table 4 shows the inhibitory spectrum on bacteria, yeasts and molds. As the medium used in the tests, GAM agar (Nissui Seiyaku, Japan) was used on lactic acid bacteria, and glucose (1%) nutrient agar was used on bacteria, yeasts and molds.

Table 3

| Indicator strains | Minimal inhibitory concentration (mcg/ml) |
|---|---|
| Streptococcus mutans HS-6 | 6.25 |
| Streptococcus mutans OMZ-61 | >100 |
| Streptococcus mutans BHT | 12.5 |
| Streptococcus mutans Ingbritt | 25 |
| Streptococcus mutans JC-2 | 50 |
| Streptococcus mutans PS-14 | 50 |
| Streptococcus mutans PK-1 | 100 |
| Streptococcus mutans GS-5 | >100 |
| Streptococcus mutans LM-7 | 25 |
| Streptococcus mutans 6715 | 100 |
| Streptococcus sanguis ATCC 10557 | 6.25 |
| Streptococcus sanguis ATCC 10558 | 6.25 |
| Streptococcus salivarius HHT | 12.5 |
| Streptococcus salivarius ATCC 9758 | 12.5 |
| Streptococcus mitis ATCC 12396 | 6.25 |
| Streptococcus bovis IFO (Institute for Fermentation, Osaka, Japan) 12057 | 6.25 |
| Streptococcus sp. CHT | 6.25 |
| Streptococcus pyogenes IID (Institute of Medical Science, University of Tokyo, Japan) 703 | 6.25 |
| (Institute of Medical Science, University of Tokyo, Japan) 715 | 6.25 |
| Lactobacillus brevis AHU (Faculty of Agriculture, Hokkaido Univ., Japan) 1509 | 50 |

Table 3-continued

| Indicator strains | Minimal inhibitory concentration (mcg/ml) |
|---|---|
| Leuconostoc mesenteroides IAM (Institute of Applied Microbiology, University of Tokyo, Japan) 1151 | 12.5 |

Table 4

| Indicator strains | Minimal inhibitory concentration (mcg/ml) |
|---|---|
| Bacillus subtilis ATCC 6633 | 6.25 |
| Staphylococcus aureus IAM 307 | 6.25 |
| Escherichia coli | >100 |
| Proteus vulgaris IFO 3851 | >100 |
| Pseudomonas fluorescens IAM 12022 | >100 |
| Serratia marcescens IFO 3046 | >100 |
| Candida utilis IAM 4264 | >100 |
| Saccharomyces carlsbergensis ATCC 9080 | >100 |
| Aspergillus niger ATCC 9642 | >100 |
| Penicillium glaucum AHU 8287 | >100 |

Furthermore, the biochemical properties of the present antimicrobial substance C-3603 are as follows. As the assay of antimicrobial activity of the present antimicrobial substance for examining the biochemical properties thereof, the overlaying method [An Old Boy's Association of Institute of Medical Science, University of Tokyo, Saikin-gaku Jisshuteiyo (Practical Summary of Microbiology) 5th edition, 1974] was used. Namely sterilized semisolid medium (pH 6.8, agar concentration 0.75%), containing 1.0% of peptone, 0.5% of yeast extract, 1.0% of sodium acetate and 1.0% of glucose, was inoculated with the indicator strain and this medium was pipetted into sterilized test tubes and after the solidification of the medium the aqueous solution of the present antimicrobial substance was overlayed by 1 ml thereon and incubated at 37° C. for 16 hours. Length of the inhibition zone produced after the incubation was measured and this length was defined as the inhibitory activity. As shown in FIG. 3, logarithm of the concentration of inhibitory substance and length of the inhibition zone (indicator strain: *Streptococcus mutans* HS-6) are in proportionate relation, so that by measuring the length of the inhibition zone the concentration of the present inhibitory substance can be assayed.

1. Heat-stability

Even if the heating treatment is performed at 100° C. for 10 minutes at pH 2, 7 and 11, the inhibitory activity does not decrease. Also, even if the heating treatment in an autoclave is performed at 121° C. for 10 minutes at pH 2, the inhibitory activity does not decrease. The results are as shown in Table 5.

Table 5

| Treatment method | Inhibitory activity (Indicator strain: *Streptococcus mutans* HS-6) |
|---|---|
| 1. pH2-Not-heat-treated inhibitory substance | 3.5 (mm) |
| 2. pH2-100° C., 10 min. Heat-treated inhibitory substance | 3.5 |
| 3. pH2-121° C., 10 min. Heat-treated inhibitory substance | 3.5 |
| 4. pH7-Not-heat-treated inhibitory substance | 3.9 |
| 5. pH7-100° C., 10 min. heat-treated inhibitory substance | 3.9 |
| 6. pH11-Not-heat-treated inhibitory substance | 3.7 |
| 7. pH11-100° C., 10 min. heat-treated inhibitory substance | 3.7 |

Note:
The inhibitory substance at pH2 and pH11 are neutralized after the heating treatment. The concentration of inhibitory substance at the time of the heating treatment is 80 mcg/ml.

2. pH-stability

The inhibitory substance is stable in the range of pH1 to pH12. The stability of the inhibitory activity in aqueous solutions at various pH is as shown in Table 6.

Table 6

| pH | Inhibitory activity (Indicator strain: *Streptococcus mutans* HS-6) |
|---|---|
| 1 | 4.1 (mm) |
| 2 | 4.1 |
| 3 | 4.0 |
| 4 | 4.0 |
| 5 | 3.9 |
| 6 | 4.0 |
| 7 | 3.9 |
| 8 | 3.9 |
| 9 | 4.0 |
| 10 | 3.8 |
| 11 | 3.8 |
| 12 | 4.0 |

Note:
The inhibitory substance adjusted to each pH (concentration 140 mcg/ml) was allowed to stand at 37° C. for 17 hours, and then it was neutralized and diluted to be a concentration of 80 mcg/ml.

3. Effect of enzyme treatment

Papain, Pronase, Pronase E, trypsin, α-chymotrypsin, lipase, phospholipase C and α-amylase were added under the conditions indicated in Table 7, and as a result the present inhibitory substance caused some loss of inhibitory activity in the cases of the α-chymotrypsin treatment and the trypsin treatment at a very high concentration of enzyme (enzyme 5,000 mcg/ml: substrate 150 mcg/ml).

Table 7

| Enzyme | Conditions of enzyme treatment | | | | | Inhibitory activity (Indicator strain: *Streptococcus mutans* HS-6) | | | |
| | pH | Temperature (°C.) | Time (min.) | Concentration of enzyme (mcg/ml) | Concentration of inhibitory substance (mcg/ml) | Inhibitory substance with no addition of enzyme | | Inhibitory substance with addition of enzyme | |
| | | | | | | Length of inhibition zone (mm) | Remaining activity (%) | Length of inhibition zone (mm) | Remaining activity (%) |
|---|---|---|---|---|---|---|---|---|---|
| Papain W-40 (Amano Pharmaceutical Co., Ltd.) | 7.0 | 37 | 70 | 10,000 | 160 | 5.0 | 100 | 5.0 | 100 |
| | 7.0 | 37 | 70 | 500 | 100 | 4.4 | 100 | 4.4 | 100 |
| Pronase (CALBIOCHEM) | 8.1 | 25 | 1,380 | 150 | 145 | 4.8 | 100 | 4.8 | 100 |
| | 8.1 | 25 | 1,380 | 50 | 145 | 4.8 | 100 | 4.8 | 100 |
| | 8.1 | 25 | 1,380 | 10 | 145 | 4.8 | 100 | 4.8 | 100 |

Table 7-continued

| Enzyme | pH | Conditions of enzyme treatment | | | | Inhibitory activity (Indicator strain: *Streptococcus mutans* HS-6) | | | |
| --- | --- | --- | --- | --- | --- | --- | --- | --- | --- |
| | | | | | | Inhibitory substance with no addition of enzyme | | Inhibitory substance with addition of enzyme | |
| | | Temperature (°C.) | Time (min.) | Concentration of enzyme (mcg/ml) | Concentration of inhibitory substance (mcg/ml) | Length of inhibition zone (mm) | Remaining activity (%) | Length of inhibition zone (mm) | Remaining activity (%) |
| Pronase E | 8.0 | 45 | 70 | 500 | 100 | 4.4 | 100 | 4.4 | 100 |
| | 8.1 | 25 | 1,380 | 150 | 145 | 4.8 | 100 | 4.8 | 100 |
| (Kaken Chemical Co., Ltd.) | 8.1 | 25 | 1,380 | 50 | 145 | 4.8 | 100 | 4.8 | 100 |
| | 8.1 | 25 | 1,380 | 10 | 145 | 4.8 | 100 | 4.8 | 100 |
| Trypsin Σ- I | 7.0 | 37 | 60 | 5,000 | 150 | 4.9 | 100 | 4.3 | 66 |
| | 7.0 | 37 | 60 | 100 | 150 | 4.9 | 100 | 4.9 | 100 |
| (Sigma Chemical Co.) | 7.0 | 37 | 60 | 50 | 150 | 4.9 | 100 | 4.9 | 100 |
| | 7.0 | 37 | 60 | 10 | 150 | 4.9 | 100 | 4.9 | 100 |
| α- Chymotrypsin | 7.8 | 28 | 400 | 200 | 150 | 4.9 | 100 | 2.4 | 17 |
| | 7.8 | 28 | 400 | 150 | 150 | 4.9 | 100 | 2.9 | 24 |
| Σ = II | 7.8 | 28 | 400 | 100 | 150 | 4.9 | 100 | 3.1 | 28 |
| | 7.8 | 28 | 400 | 50 | 150 | 4.9 | 100 | 3.9 | 49 |
| (Sigma Chemical Co.) | 7.8 | 28 | 400 | 50 | 150 | 4.9 | 100 | 3.9 | 49 |
| | 7.8 | 28 | 400 | 10 | 150 | 4.9 | 100 | 3.9 | 49 |
| Lipase M-AP-10 | 7.0 | 37 | 60 | 5,000 | 150 | 4.9 | 100 | 4.9 | 100 |
| (Amano Pharmaceutical Co., Ltd.) | 7.0 | 37 | 70 | 500 | 100 | 4.4 | 100 | 4.4 | 100 |
| Phospholipase C | 7.0 | 37 | 70 | 500 | 100 | 4.4 | 100 | 4.4 | 100 |
| (Sigma Chemical Co.) | 7.0 | 37 | 60 | 375 | 150 | 4.9 | 100 | 4.9 | 100 |
| α- Amylase | 7.0 | 37 | 70 | 500 | 100 | 4.4 | 100 | 4.4 | 100 |
| | 7.0 | 25 | 1,380 | 150 | 145 | 4.8 | 100 | 4.8 | 100 |
| (Tokyo Kasei Kogyo Co., Ltd.) | 7.0 | 25 | 1,380 | 50 | 145 | 4.8 | 100 | 4.8 | 100 |
| | 7.0 | 25 | 1,380 | 10 | 145 | 4.8 | 100 | 4.8 | 100 |

Note:
The remaining activity was shown by percentage to the activity of inhibitory substance with no addition of enzyme, on the basis of concentration obtained by the graph of FIG. 3.

As the reports in which substances similar to the antimicrobial substance C-3603 obtained by the present invention are reported, there are report of J. R. Tagg et al. (J. Exp. Med., 138, 1168, 1973), that of D. Paul and H. D. Slade (Infect. Immun., 12, 1375, 1975), that of T. Yamamoto et al. (Archs oral Biol., 20, 389, 1975) and that of Katsuyuki Futakami (Japanese Patent Publication of Application laid open to public inspection No. 44296/77). However the substance reported by J. R. Tagg et al. is completely inactivated under alkaline conditions above pH 11, on the contrary the present antimicrobial substance C-3603 causes no loss of inhibitory activity. Moreover, by the addition treatments of Pronase and trypsin it is completely inactivated, but the present antimicrobial substance C-3603 causes no loss of inhibitory activity by Pronase and is remarkably tolerant to trypsin as shown in Table 7.

Moreover, the substance reported by J. R. Tagg et al. does not show any inhibitory activity against *Staphylococcus aureus*, but the present antimicrobial substance C-3603 shows an inhibitory activity against it.

The substance reported by D. Paul et al. has a molecular weight above 20,000, but the present antimicrobial substance C-3603 has that of 6,000–10,000. Also, although the substance of D. Paul et al. is completely inactivated at pH 11, the present antimicrobial substance C-3603 is not inactivated at that pH. Also, by the addition treatments of Pronase, phospholipase C and trypsin it is completely inactivated, but the present antimicrobial substance C-3603 is not inactivated by the addition treatments of Pronase and phospholipase C and is remarkably tolerant to trypsin as shown in Table 7.

Moreover, relating to the inhibitory spectrum, the substance reported by D. Paul et al. does not show any inhibitory activity against *Streptococcus mutans* BHT and JC-2 and against *Bacillus subtilis*, but the present antimicrobial substance C-3603 shows an inhibitory activity against them.

The substance reported by T. Yamamoto et al. is completely inactivated by the addition treatment of Pronase E and in the inhibitory spectrum it does not show an inhibitory activity against *Streptococcus mitis* ATCC 12396 and Streptococcus CHT, but the present antimicrobial substance C-3603 is not inactivated by the addition treatment of Pronase E as shown in Table 7 and shows an inhibitory activity against said two strains.

There is the description in said Japanese Patent Application Publication No. 44296/77 that the inhibitory substance is a neutral substance according to the item of physical and chemical properties, on the contrary the present antimicrobial substance C-3603 is a basic substance having an isoelectric point of 10.0±0.2. Also, there is described that it is inactivated approximately completely by the addition treatment of lipase and suggested that it contains lipid as the active site of inhibitory substance, but the present antimicrobial substance C-3603 causes no loss of inhibitory activity by lipase as shown in Table 7 and as well fatty acids ($C_{10}$–$C_{18}$) are not detected as shown in the results of the analysis of fatty acids. Relating to the inhibitory spectrum, a comparison between the inhibitory activity of the present antimicrobial substance C-3603 and that reported in said Patent Application, shows that there are some differences in the inhibitory activity against *Streptococcus mutans* GS-5, 6715, PK-1, PS-14 and OMZ-61 used as test strains.

A comparison between the descriptions above described shows that the present antimicrobial substance C-3603 is apparently different from said analogous substances. Accordingly, the antimicrobial substance C-3603 obtained by the present invention has been concluded to be a novel antimicrobial substance.

In order to examine in vitro the preventive effect of dental caries of the present antimicrobial substance C-3603, culture tests for examining the production of adhesive polysaccharide have been carried out. Namely, 10 ml of liquid medium (pH 6.8) containing 2.0% of peptone, 0.2% of NaCl, 0.3% of $K_2HPO_4$, 0.2% of $KH_2PO_4$, 0.1% of $K_2CO_3$, 0.012% of $MgSO_4.7H_2O$, 0.0015% of $MnSO_4.4$–$6H_2O$, 10% of sucrose, and various amount of the present antimicrobial substance C-3603, is inoculated with cariogenic bacteria or fresh dental plaque collected from an oral cavity of human being, and a stainless wire of a diameter of 0.8 mm fixed by insertion into a cotton plug is dipped in the medium. After an anaerobic culture at 37° C. for one day, this stainless wire is transferred in a fresh medium in which cariogenic bacteria or dental plaque has been inoculated, and such culture is repeated. Such operations are repeated for ten days and then an amount of the insoluble polysaccharide adhered to the stainless wire is determined. At the same time, the growth condition of microorganism is examined by observation of turbidity of the culture liquid with the naked eyes and measurement of pH thereof. The results thereof are as shown in Table 8.

Table 8

| Streptoccus strain or dental plaque | Concentration of the antimicrobial substance (mcg/ml) | Observation with the naked eyes | pH of liquid after culturing | Polysaccharide adhered to stainless wire (mg) |
|---|---|---|---|---|
| Streptococcus salivarius HHT | 0 | + | 4.5 | 6.68 |
| | 2.5 | + | 4.6 | 4.90 |
| | 25 | − | 6.6 | 0.04 |
| | 50 | − | 6.6 | 0.03 |
| Dental plaque | 0 | + | 4.2 | 6.44 |
| | 2.5 | + | 4.2 | 7.15 |
| | 25 | + | 4.3 | 0.94 |
| | 50 | + | 4.3 | 0.06 |

Note:
Observation by the naked eyes: + abundant growth,
− no growth is recognized.
An amount of polysaccharide is represented by a conversion into amount of glucose by use of phenol-sulphuric acid method.

In the case of *Streptococcus salivarius HHT*, the growth was remarkably prevented at a concentration of inhibitory substance of above 25 mcg/ml, and the quantity of polysaccharide adhered to the stainless wire was remarkably reduced compared with the control (the concentration of inhibitory substance of 0 mcg/ml). In the case of dental plaque of person, the prevention of growth was not observed even at a concentration of inhibitory substance of above 25 mcg/ml, but the quantity of adhesive polysaccharide fairly reduced more than in the control. As a result, the present antimicrobial substance C-3603 is recognized to have an effect to prevent the production of polysaccharide which is supposed to be a cause of dental caries, and therefore it is expected that said substance can be used effectively for the prevention of dental caries. As a method of utilization for prevention and medical treatment of dental caries, the present antimicrobial substance C-3603 can be used as an effective component in tooth paste, a medicine applied in oral cavity, gargle, ointment, chewing gum, troche or general foodstuffs etc. Moreover, the present antimicrobial substance C-3603 has a specific inhibitory spectrum, so that other various utilizations can be expected. For example, it has a strong inhibitory activity against *Streptococcus pyogenes*, and accordingly it may be used for the prevention and medical treatment of acute rheumatic fever and scarlet fever which are infectious diseases caused by *Streptococcus pyogenes*.

The following practical examples of the present invention are illustrative but not limitative of the present invention.

PRACTICAL EXAMPLE 1

*Streptococcus mutans* C-3603, FERM-P No. 4128 and ATCC No. 31383 was inoculated into 100 ml of the liquid medium (pH 7.7) containing 1.0% of glucose, 2.0% of peptone, 0.5% of NaCl, 0.3% of $K_2HPO_4$, 0.2% of $KH_2PO_4$, 0.01% of $MgSO_4.7H_2O$ and 0.002% of $MnSO_4.4$–$6H_2O$, and the static culture was carried out under the aerobic condition at 37° C. for one day. The resulting culture liquid was inoculated in 10 l of same medium as described above and this was subjected to a static culture at 37° C. for 20 hours under the aerobic condition. The culture liquid thus obtained was continuously centrifuged at 20,000 G to give a supernatant fluid. Next, this supernatant fluid was added with 3.8 kg of ammonium sulfate and allowed to stand at about 5° C. for one night. Thus formed precipitation was collected by a continuous centrifugation at 20,000 G. Thus obtained precipitation was dissolved in a small amount of phosphate buffer solution ($10^{-2}$ mol, pH 7.0), and thereafter the resulting solution was centrifuged at 12,000 G for 10 min. to remove the precipitation. Thus obtained supernatant solution was passed through a column (5.0×30 cm) filled with CM-Sephadex C-25 which had been previously bufferized by the same buffer solution and thereby the inhibitory substance was adsorbed thereon, and then the same buffer solution was further passed through the column to wash it thoroughly.

Next, after washing by passing a solution adjusted to pH 9.5 by addition of sodium hydroxide to phosphate buffer solution (5×$10^{-2}$ mol, pH 7.0), a buffer solution of pH 10.8 adjusted likewise by the addition of sodium hydroxide was passed to elute the inhibitory substance. The eluted solution was passed through the Sephadex G-25 column (5.5×80 cm) so as to be deionized, and the obtained inhibitory substance solution was freeze-dried to yield about 80 mg of a white purified inhibitory substance. The antimicrobial substance purified by this method showed a single band in the polyacrylamide gel disc electrophoresis (polyacrylamide 15%, pH 2.3 gel).

PRACTICAL EXAMPLE 2

To 10 l of the supernatant fluid obtained in the same manner as Practical example 1, 40 l of deionized water was added. Thus obtained diluted supernatant fluid was passed through CM-Sephadex C-25 column (5.0×30 cm) which had been previously bufferized by phosphate buffer solution ($10^{-2}$ mol, pH 7.0), thereby the inhibitory substance was adsorbed thereon, and the same buffer solution was further passed through the column to wash it thoroughly.

Next, after washing by passing a solution adjusted to pH 8.0 by addition of sodium hydroxide to phosphate buffer solution (5×$10^{-2}$ mol, pH 7.0), and phosphate buffer solution ($10^{-2}$ mol, pH 7.0) containing 3% of NaCl was passed to elute the inhibitory substance. The eluted solution was passed through the Sephadex G-25 column (5.5×80 cm) so as to be deionized, and the obtained inhibitory substance solution was freeze-dried to yield about 140 mg of a white purified antimicrobial substance.

By the way the antimicrobial substance purified by this method showed a single band in the polyacrylamide gel disc electrophoresis (polyacrylamide 15%, pH 2.3 gel).

What is claimed is:

1. An antimicrobial substance C-3603 having the following physical and chemical properties:
   (1) Molecular weight
      6.000–10.000 (determined by SDS-polyacrylamide gel disc electrophoresis);
   (2) Decomposition point
      190°–195° C.;
   (3) Ultraviolet absorption spectrum
      in aqueous solution as shown in FIG. 1 having absorption maxima at 280 nm ($E_{1\ cm}^{1\%}$: 40) and 289 nm ($E_{1\ cm}^{1\%}$: 33);
   (4) Infrared absorption spectrum
      shown in FIG. 2 as measured by KBr pellet method and having absorption bands at the following wave numbers expressed in reciprocal centimeters: 3290, 1650, 1535, 1240, 1105, 733;
   (5) Solubility to solvent
      slightly soluble in aqueous solution of acid (pH 3.0), and practically insoluble in water; insoluble in methanol, ethanol, acetone, ether, acetic acid ethyl ester, chloroform, n-hexane and benzene;
   (6) Color reaction
      reacts positively in the following color reactions: ninhydrin, biuret, xanthoprotein and Adamkiewicz;
   (7) Isoelectric point
      pI=10.0±0.2 (determined by polyacrylamide gel disc isoelectric separation);
   (8) Color and form of substance
      White powder;
   (9) Analysis of amino acids
      by p-toluenesulfonic acid hydrolysis, the following amino acids are found: aspartic acid, threonine, serine, glutamic acid, glycine, alanine, valine, methionine, isoleucine, leucine, tyrosine, phenylalanine, tryptophan, lysine, ammonia and arginine, but the following are not found: proline, cysteine and histidine.
   (10) Elemental analysis
      (i) C: 50.01%, H: 6.19%, N: 12.84%, S: 0.96%, O (balance): 30.00%
      (ii) C: 49.80%, H: 6.30%, N: 11.41%, S: 1.18%; O (balance): 31.31%; and
   (11) Analysis of fatty acids
      hydrolysate by acid (6 N HCl, 120° C., 20 hr.) extracted by chloroform-methanol, but the fatty acids ($C_{10}$–$C_{18}$) not detected by gas-liquid-chromatography.

2. A process for preparing the antimicrobial substance C-3603 as defined in claim 1, which comprises cultivating *Streptococcus mutans* C-3603 (ATCC No. 31383) producing the antimicrobial substance C-3603 in an aqueous nutrient medium until substantial antibiotic activity is imparted to said medium under the conditions of initial pH 5~9 and temperature 20°–40° C., and recovering the accumulated antimicrobial substance C-3603 from the culture fluid.

* * * * *